(12) United States Patent
Triplett et al.

(10) Patent No.: US 7,681,806 B2
(45) Date of Patent: Mar. 23, 2010

(54) VAPOR DISPERSING DEVICE AND METHOD

(75) Inventors: Carl Triplett, Scottsdale, AZ (US); Paul Pappalardo, Scottsdale, AZ (US); Mengato Pete He, Scottsdale, AZ (US); David Hunt, Cincinnati, OH (US); Gilbert Schmidt, Cincinnati, OH (US)

(73) Assignee: The Dial Corporation, Scottsdale, AZ (US)

( * ) Notice: Subject to any disclaimer, the term of this patent is extended or adjusted under 35 U.S.C. 154(b) by 1325 days.

(21) Appl. No.: 10/900,474

(22) Filed: Jul. 28, 2004

(65) Prior Publication Data
US 2006/0022064 A1 Feb. 2, 2006

(51) Int. Cl.
*A24F 25/00* (2006.01)
*A61L 9/04* (2006.01)

(52) U.S. Cl. ............................ 239/47; 239/44; 239/45; 239/55; 239/42; 239/142; 222/187

(58) Field of Classification Search .................. 239/44, 239/45, 47, 49, 50, 51.5, 53, 58; 222/180, 222/187
See application file for complete search history.

(56) References Cited

U.S. PATENT DOCUMENTS

| | | | |
|---|---|---|---|
| 1,332,659 A | 3/1920 | Bates | |
| 2,383,960 A | 9/1945 | Dupuy et al. | |
| 2,975,464 A | 3/1961 | Schultz | |
| 3,587,968 A | 6/1971 | Hennart et al. | |
| D253,549 S | 11/1979 | Seager | |
| 4,413,779 A | 11/1983 | Santini | |
| 4,419,326 A * | 12/1983 | Santini | 422/4 |
| 4,621,768 A | 11/1986 | Lhoste et al. | |
| D289,565 S | 4/1987 | Mann | |
| 4,732,321 A * | 3/1988 | Dolan | 239/45 |
| 4,739,928 A | 4/1988 | O'Neil | |
| D306,478 S | 3/1990 | von Philipp et al. | |
| 4,928,881 A | 5/1990 | Barlics et al. | |
| 5,000,383 A * | 3/1991 | van der Heijden | 239/47 |
| 5,014,913 A | 5/1991 | Hoyt et al. | |
| D320,739 S | 10/1991 | Camus | |
| D321,930 S | 11/1991 | Dinand | |
| 5,077,102 A | 12/1991 | Chong | |
| 5,219,121 A | 6/1993 | Fox et al. | |
| 5,242,111 A | 9/1993 | Nakoneczny et al. | |

(Continued)

FOREIGN PATENT DOCUMENTS

DE          4237892 C2          5/1994

(Continued)

*Primary Examiner*—Dinh Q Nguyen
(74) *Attorney, Agent, or Firm*—Paul A. Pappalardo (57) ABSTRACT

A passive vapor dispersing device which may be used for freshening or otherwise treating the air, characterized by both rapid and substantially linear delivery of volatizable fragrance or other materials. The device uses a packaged combination of liquid reservoir, wick and emanator which is assembled and shipped with the wick and emanator out of contact with each other, but is activated when the user opens the package and places the wick and emanator in contact. The housing for the device provides guide means for assisting the user in placing the wick and emanator in proper contact, and irreversible lock means for holding the components in contact and preventing access to the wick and emanator once activation has been achieved.

9 Claims, 9 Drawing Sheets

U.S. PATENT DOCUMENTS

| | | |
|---|---|---|
| D355,251 S | 2/1995 | Paulovich et al. |
| D380,257 S | 6/1997 | Ganor |
| D393,063 S | 3/1998 | Wefler |
| 5,725,152 A * | 3/1998 | Akyu .................... 239/45 |
| 5,776,561 A | 7/1998 | Lindauer |
| D406,885 S | 3/1999 | Jane' et al. |
| 5,909,845 A | 6/1999 | Greatbatch et al. |
| D432,223 S | 10/2000 | King |
| 6,354,513 B1 | 3/2002 | Millan |
| 6,383,165 B1 | 5/2002 | Maget |
| 6,391,398 B1 | 5/2002 | Pesu et al. |
| D458,848 S | 6/2002 | Tompkins |
| D459,230 S | 6/2002 | Tompkins |
| 6,446,880 B1 | 9/2002 | Schram et al. |
| 6,513,726 B1 | 2/2003 | Esteban Duran |
| 6,555,069 B1 * | 4/2003 | Ferguson .................... 422/126 |
| 6,565,012 B1 | 5/2003 | Zaragoza et al. |
| RE38,150 E | 6/2003 | Greatbatch et al. |
| 6,667,006 B2 | 12/2003 | Richards |
| 6,698,665 B2 | 3/2004 | Minamite et al. |
| 6,699,432 B2 | 3/2004 | Channer |
| 6,708,897 B1 | 3/2004 | Hart et al. |
| D488,214 S | 4/2004 | Quantin |
| 2002/0136886 A1 | 9/2002 | He et al. |
| 2002/0168301 A1 | 11/2002 | Channer |
| 2003/0071137 A1 | 4/2003 | Giovannone |
| 2003/0098362 A1 | 5/2003 | Chuang |
| 2003/0132308 A1 | 7/2003 | Vieira |
| 2003/0146294 A1 | 8/2003 | Minamite et al. |
| 2003/0161755 A1 | 8/2003 | Richards |

FOREIGN PATENT DOCUMENTS

| | | |
|---|---|---|
| EP | 0028852 A1 | 5/1981 |
| EP | 0134360 A1 | 3/1985 |
| EP | 0501601 B1 | 4/1994 |
| EP | 0669137 A1 | 8/1995 |
| EP | 1220692 B1 | 2/2004 |
| GB | 2181649 A | 4/1987 |
| GB | 2355200 A | 4/2001 |
| GB | 2357973 A | 7/2001 |
| GB | 2370225 A | 6/2002 |
| WO | WO 97/26926 A1 | 7/1997 |
| WO | WO 02/30220 A1 | 4/2002 |
| WO | WO 03/101499 A1 | 12/2003 |
| WO | WO 2004/084958 | 3/2004 |

* cited by examiner

VAPOR DISPERSING DEVICE AND METHOD

FIELD OF INVENTION

This invention generally relates to vapor-dispersing devices, and more particularly, to a passive vapor-dispersing device having a prolonged high-intensity and substantially linear dispersion of vapor, along with a unique activation and safety mechanism.

BACKGROUND OF INVENTION

Vapor-dispersing apparatuses for volatizing a liquid in a container to a vapor in the atmosphere have been known in the art for many years. Passive vapor-dispersing apparatuses typically include a volatizable material in communication with a material delivery system configured to facilitate evaporation of the volatizable material into the air of the surrounding environment at ambient conditions, i.e., without significant mechanical or electrical assistance such as spraying or heating. In some delivery systems, the vaporizer includes a liquid such as oil contained in a reservoir; in others, the vaporizer includes a wax, gel, or other such solid or colloidal material.

In particular, many of these devices make use of the principle of diffusion. For instance, some devices make use of a wick-based system. In these systems, one end of a wick is placed in a fluid to be volatized, while the other end is exposed to the atmosphere. Capillary action forces liquid through the wick and up to the exposed end, where the liquid evaporates off of the end of the wick and into the surrounding atmosphere.

By virtue of the passive nature of such vaporizers, the rate at which vapor is delivered to the environment starts at a very low level when the device is first activated (e.g., removed from the packaging), then slowly levels-off to a relatively low steady state value. In non-vented systems, a partial vacuum can even develop in the reservoir causing the capillary action to seriously slow down. It would be advantageous for passive vapor-dispersing devices, such as room deodorizers and the like, to provide, a relatively linear level of vaporization over the lifetime of the product, and to have rapid activation.

Wick type dispersers have more disadvantages. Wick type dispersers typically comprise either a one-piece or two-piece wick. In the two-piece wick device, for example, the wick may be used to conduct fluid into a secondary emanator or second wick portion, where the fluid vaporizes. Both one-piece and two-piece wick systems suffer inherent problems. The one piece wick is either molded from a single block of porous plastic, making the part overly expensive, or the one-piece wick is a simple and cheap fibrous bundle of material which cannot be effectively sealed to the neck of the fluid reservoir and kept from dripping at this connection or even from the material itself, causing a serious safety hazard and mess for the consumer. Furthermore, for the two-piece wick system, such as a wick-to-emanator system, there is little in the prior art to suggest how the user is to connect the conduit wick to this secondary emanator, in fact, in most instances, it is assumed this connection is already made at the time of manufacturing.

A pre-activated wick-to-emanator system has many drawbacks. First is the need for an enormous closure to seal both the wick and the pre-saturated emanator, which would be an expensive molded plastic part. Second, the consumer could easily touch the pre-saturated emanator and in some instances, this could be a safety issue. For a vapor-dispersing apparatus to vaporize a strong concentration of active material, the volatizable material should preferably be a very concentrated material, in fact, most preferably close to 100% active material. In the case where the vapor-dispersing apparatus is an air freshener for example, the volatizable material should preferentially be essentially 100% pure fragrance oil with only small amounts of solvent carrier.

Obviously, concentrated or near 100% active organic compositions such as fragrance oils or insecticides may be severe eye and skin irritants, and it would be advantageous to have a safe way for the consumer to activate any vapor-dispersing apparatus. In particular, in the case of a wick-to-pad system designed to vaporize a potentially unsafe material, it is essential that a safe way to activate the apparatus be invented. More specifically, what is needed is a method for the user to activate a wick-to-pad vapor-dispersing apparatus and then not be able to access the inside of the apparatus and touch the activated and saturated pad, for the life of the product.

SUMMARY OF INVENTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth in the appended claims. For example, in the context of the present invention, the method and apparatus hereof find particular use in connection with air freshening vaporizer systems. However, generally speaking, various volatizable materials such as deodorizers, sanitizers, insecticides and medicaments and/or the like are suitable for use in accordance with the present invention. Likewise, though various portions of the specification refer to high intensity scented oils as the volatizable material used herein, various other materials now known or as yet unknown, having similar properties should be considered within the scope of the present invention.

Briefly, the term "high intensity" may be characterized in various different ways including human perception, rates of dispensation, insecticidal efficacy, range of coverage, and/or the like. For example, high intensity may be defined through testing of fragrance perception in a group of people. The intensity may include such factors as the ability to overcome certain odors. Other systems for characterizing high intensity volatization may include the amount of volatizable material dispersed over a period of time. For example, a high intensity fragrance material might comprise one or more of various scented oils.

A passive vapor-dispersing apparatus in accordance with the present invention generally comprises a housing containing a material delivery device with volatizable material and a method to activate the apparatus, use it, handle it and dispose of it, all in a safe manner. In accordance with another aspect of the present invention, a vapor-dispersing apparatus is characterized by prolonged, high-intensity operation and a rapid ramp-up to the high-intensity operation upon activation by the user.

The present invention comprises a vapor-dispersing apparatus further comprising an enclosure with housing portions and at least one vent, a volatizable material delivery system, and a fastening means to connect together the various housing portions of the enclosure and activate the apparatus in the process of assembling the enclosure.

BRIEF DESCRIPTION OF THE DRAWING FIGURES

Additional aspects of the present invention should become evident upon reviewing the non-limiting embodiments described in the specification taken in conjunction with the accompanying figures, wherein like numerals designate like elements, and.

DETAILED DESCRIPTION

The description that follows is not intended to limit the scope, applicability or configuration of the invention in any way; rather, it is intended to provide a convenient illustration for implementing various embodiments of the invention. As will become apparent, various changes may be made in the function and arrangement of the elements described in these embodiments without departing from the scope of the invention.

For example, the methods and apparatus described herein find particular use in connection with air freshening vaporizer systems. Generally speaking, however, a variety of other volatizable materials such as insect repellents, deodorizers, sanitizers, and the like may be suitable for use in accordance with the present invention.

Figure 1:
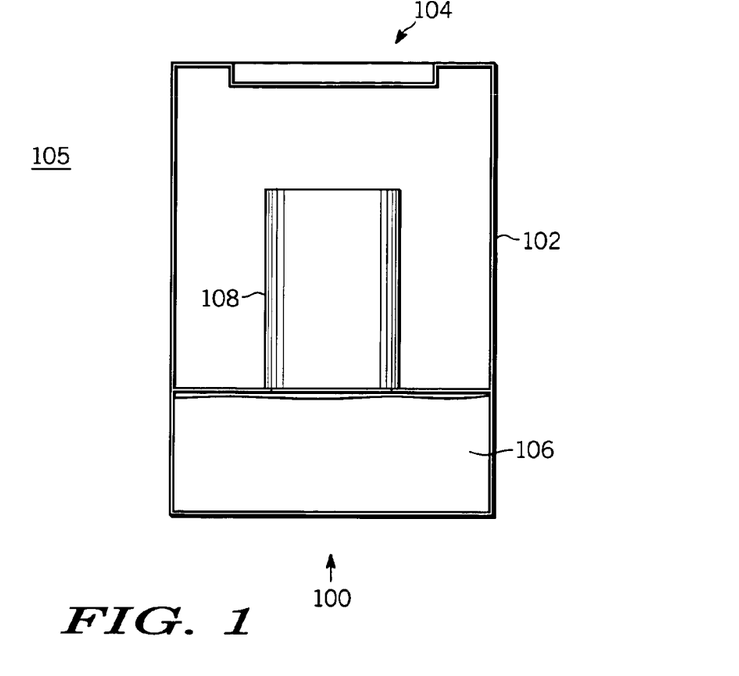
FIG. 1-3 are conceptual cross-sections of an exemplary vapor-dispersing apparatus in accordance with one embodiment of the present invention.

With reference to the conceptual cross-sectional illustration shown in FIG. 1, a passive vapor-dispersing apparatus 100 in accordance with various aspects of the present inventions includes an enclosure 102 containing a volatizable material 106 and at least one vent 104 somewhere on the enclosure 102. A material delivery system 108, housed inside enclosure 102, communicates with volatizable material 106 and facilitates its transport and/or evaporation through at least one vent 104 into an environment 105.

In the context of an air freshener, volatizable material 106 comprises any suitable high intensity fragrance emitting substance. In one exemplary embodiment, volatizable material 106 comprises scented oil. Various rates of dispensation of fragrance material may characterize high intensity fragrance. Such rates may depend on the type of fragrance, pungency of the fragrance, the material delivery system performance, and/or other factors. In this example, volatizable material 106 may be configured to emit fragrance material at a rate of 5 to 50 milligrams per hour, and preferably at a rate of 10-40 milligrams per hour, and most preferably at a rate of 18 milligrams per hour. Other rates may similarly characterize high intensity fragrance as the intensity may also depend on the type of fragrance, pungency of the fragrance, the material delivery system performance, and/or other factors in addition to the rate of material delivery. Other high intensity fragrance emitting substances may also be used in the present invention.

Figure 2:
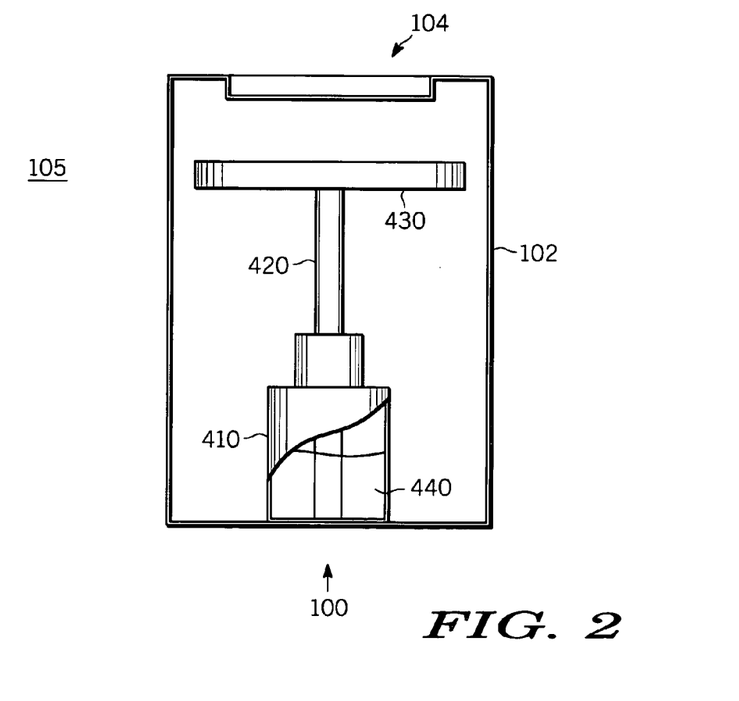

Various exemplary material delivery systems are configured to convey volatizable material 106 to the surrounding environment and are particularly well suited for high intensity scented oils. FIG. 2 illustrates one arrangement to which the material delivery system 108 shown in FIG. 1 comprises a reservoir 410, wick 420, and emanator 430. Reservoir 410 is configured to hold a volatile material such as fragrance oil 440. Briefly, reservoir 410 comprises any structure capable of holding a scented liquid (such as a scented oil) and small enough to be practical. For example, reservoir 410 may be a glass or blow-molded plastic bottle.

Wick 420 is configured to receive volatizable material 440 and to facilitate the conduction of the material into the emanator 430. Emanator 430 facilitates dispersion of the material to the surrounding environment. For example, wick 420 and emanator 430 together are configured to draw volatizable material into a region that is exposed to the surrounding environment. Therefore, emanator 430 receives volatizable material through such mechanisms as the wicking of volatizable material 440 from reservoir 410, through wick 420. Wick 420 is made, for example, of a porous material such as graphite, porous plastic or other fibrous materials. Particularly preferred wick materials include porous polymeric wicks having pore sizes less than about 250 microns and void volume ratios from about 25 to about 60 percent, such as are described in U.S. Patent Application Publication 2002/0136886 entitled "Porous Wick for Liquid Vaporizers", filed Oct. 9, 2001, the subject matter of which is hereby incorporated herein by reference. Preferred pore sizes are from about 20 microns to about 100 microns. In one exemplary embodiment, wick 420, is a porous plastic wick with a pore size of 45 micron, a void volume of about 40-45% and a diameter of about 1 cm.

Emanator 430 is made, for example, of an absorptive, porous material such as cellulose, non-woven, ceramic, porous plastic, compressed polymer fibers, blotter board, wood, and the like. The emanator 430 can virtually be of any size, however it needs to be practically sized. For example, if the emanator 430 were enormous, it would simply draw the entire contents of reservoir 410 into its interstices. Additionally, the entire vapor-dispersing apparatus needs to be of a practical size. Thus, the preferred size for the emanator 430 is from about 0.5 square inch to about 20 square inches, depending on the nature and amount of volatizable material 106 and the size of reservoir 410 that contains it. In examples where the amount of volatizable material is perhaps about 10 to about 50 grams, the most preferred and practical size for the emanator 430 is from about 1 to about 2 square inches. Obviously the emanator 430 need not be square shaped; rather it could be circular, oval, etc., or whatever is appropriate for the application and the overall look of the apparatus. Additionally, the emanator 430 need not be flat. It can be curved, fluted, etc., to maximize surface area, evaporative performance, airflow, and the like.

Preferred emanator materials are the porous plastic sheets and the cellulose adsorbent carrier (AC) sheets. Examples of the preferred porous plastic sheets are polyethylene or high density polyethylene porous plastic sheets, measuring from about 1/16 inch thickness to about 1/4 inch thickness, having pore size from about 15 to about 130 microns. For example, porous plastic sheet X-4900 from POREX, a 1/16$^{th}$ inch thick 15-45 micron pore size sheet would work well in the present invention. Most preferred emanator materials are the adsorbent carrier (AC) cellulose sheets. For example, the AC-16 cellulose materials from FM Specialty Products represent emanator materials that work well in the present invention. Thickness for the AC-16 material may range from about 1/16 inch thick to about 1 inch thick. Preferred thickness is from about 1/8 inch to about 1/2 inch thick. Most preferred thickness is from about 1/8 inch to about 3/8 inch.

As a consequence of the efficiency of the wicking ability of wick 420, i.e., its ability to conduct liquid via capillary action, and the absorptive capacity of emanator 430, the emanator will be quickly and completely saturated with volatizable material 440 within a substantially short time after the wick 420 is brought into contact with the emanator 430. As mentioned above, porous plastic can be expensive, thus it is advantageous to limit the size of wick 420, if it is to be molded from porous plastic, and to maximize the size of the emanator 430, if it is to be inexpensive adsorbent carrier (AC) cellulose, in order to ensure efficiency of volatilization of material into the environment. Emanator 430 will draw as much volatizable material 440 into its matrix as it can, and for some emanator materials such as cellulose, this initial draw of material into the emanator can be substantially large. Of course, the absorbed liquid capacity of the emanator is a function not only of the material it is made from, but also the size and thickness of it. Maximizing the size of the emanator 430 necessarily maximizes the initial draw of volatizable material 440 from reservoir 410.

When wick 420 is brought into contact with emanator 430, volatizable material 440 is rapidly conducted from reservoir 410 into emanator 430, resulting in a substantially saturated emanator 430 from which vapor can be passively delivered to the environment. In this regard, "passive delivery" refers to and includes delivery without substantial mechanical and/or electrical assistance (e.g., heating elements, fans, and the like).

Passive delivery systems include, for example, vaporizers that deliver material to the environment via mass transport of volatized compounds at one or more surfaces under free convection boundary conditions and/or forced convection produced by the movement of air within the environment.

Figure 3:
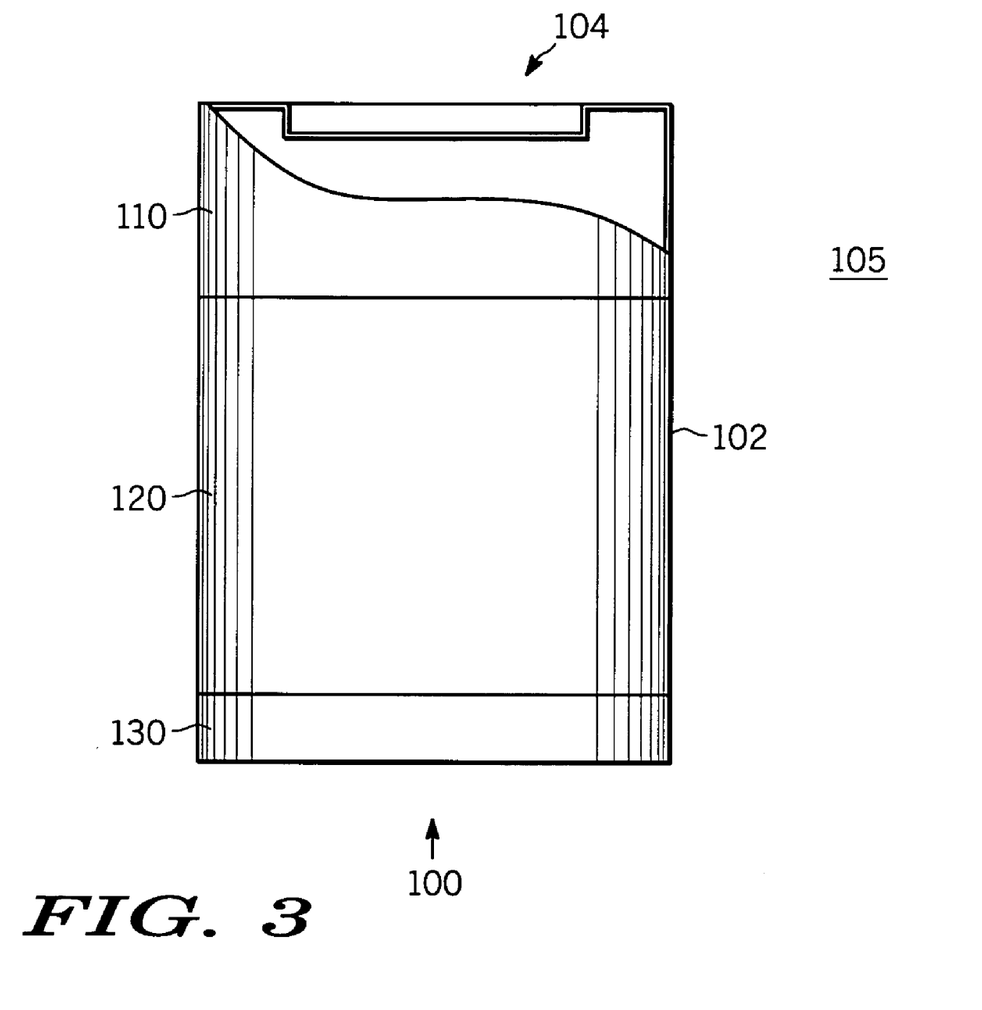

With reference to the drawing in FIG. 3, Enclosure 102 may comprise any suitable material (e.g., various plastics, composites, paperboard, or the like). Enclosure 102 may include, for example, a base (i.e., for providing stability on flat surfaces) and various other internal components and structural engineering configured to support material delivery system 108. Also, enclosure 102 may comprise a viewing feature to allow visual connection to the interior. For example, an "end of life indicator" may be as simple as a viewing window positioned somewhere on the enclosure 102 that allows view of the material delivery system 108. Most preferred is a cutaway section of the base of enclosure 102 that allows view of the bottom of reservoir 410 when the apparatus is inverted. As depicted in conceptual illustration FIG. 3, enclosure 102 may comprise multiple parts that require assembly by the manufacturer, the user, or more preferably, by both. In one exemplary embodiment, enclosure 102 is comprised of at least three separate housing portions, for example, top 110, middle 120 and bottom 130 housing portions.

Volatizable material 106 comprises any of the various volatizable materials which currently exist and/or are hereafter devised by those skilled in the art, for example, insect repellents, deodorizers, sanitizers or the like. In the illustrated embodiment, the volatizable material comprises a fragrance material in the form of a liquid, wax, or other convenient substance. In a preferred embodiment, volatizable material 106 is a liquid comprising an oil-based liquid fragrance, and this liquid may be either of low viscosity or purposely thickened, for example with inorganic or polymeric viscosity modifiers.

The liquid fragrance component used in forming volatizable material 106 preferably comprises an oil and/or perfume necessary to provide the desired perfume fragrance. Other agents may be used in conjunction with the fragrance component. For example, known materials such as solvents and surfactants and the like can be employed without departing from the scope of the present invention.

In any event, the liquid fragrance ingredient preferably comprises one or more volatile organic compounds available from any of the now known or hereafter developed perfumery suppliers, such as International Fragrance and Flavors, Givaudan, Firmenich, etc. Many types of fragrances can be used in the present invention. Preferably, the fragrance materials are volatile essential oils. The fragrance, however, can be synthetically formed material, naturally derived oil, or mixtures thereof. Naturally derived oils include, but are not limited to, Bergamot, Bitter Orange, Lemon, Mandarin, Caraway, Cedarleaf, Clove leaf, Cedar wood, Geranium, Lavender, Orange, Origanum, White Cedar, Lavender, Rose Absolute and the like. Suitable fragrances include but are not limited to fruits, musk, flower scents, herbal scents, woodland scents, derived from pine, spruce and other forest smells. Fragrances may be derived from various oils such as the foregoing essential oils or from plant materials such as peppermint, spearmint and the like.

The total lifetime of the vapor-dispersing apparatus depends upon a number of factors, including the mass of total volatizable material 106, the nature of material delivery system 108, and various attributes of volatizable material 106, (e.g., flashpoint, distribution of volatile components, such as high middle and base notes in a perfume composition, and the like). For purposes of further describing the invention, the term "initial evaporation rate" for the volatizable material is the amount of material vaporized in about the first day or so. The term "steady state evaporation rate" is defined to be that rate experienced throughout most of the life of the apparatus. In one embodiment, the steady state evaporation rate is between approximately 10 mg/hr (milligrams per hour) and 50 mg/hr, preferably between 15 mg/hr and 30 mg/hr, and most preferably about 18 to about 20 mg/hr. The total lifetime of the product is preferably between approximately 30 days and 60 days, and most preferably about 45 days (e.g., at a steady state evaporation rate of approximately 18 mg/hr and a reservoir fill of about 19 grams of volatizable material, the product is expected to last about 45-days).

The rate of evaporation of volatizable material can be changed by the nature of the material delivery system 108. For example, the choice material for the emanator 430, and especially the size of the emanator 430, and the configuration and size of the vent or vents 104, will define the evaporation rate for the volatizable material 440. What is not a factor is the nature of the wick 420. For this invention, wick 420 functions only as the pipeline between the reservoir 410 and the emanator 430, and it is preferable that wick 420 supply an unlimited amount of volatizable material 440 to maintain a substantially saturated emanator 430 until the reservoir 410 is depleted of volatizable material 440. In this manner, when wick 420 is connected to emanator 430, the vapor-dispersing apparatus comes quickly up to the steady state evaporation (i.e., a rapid activation or saturated emanator 430) and then delivers volatizable material 440 substantially linearly from this saturated emanator 430.

Figure 4:
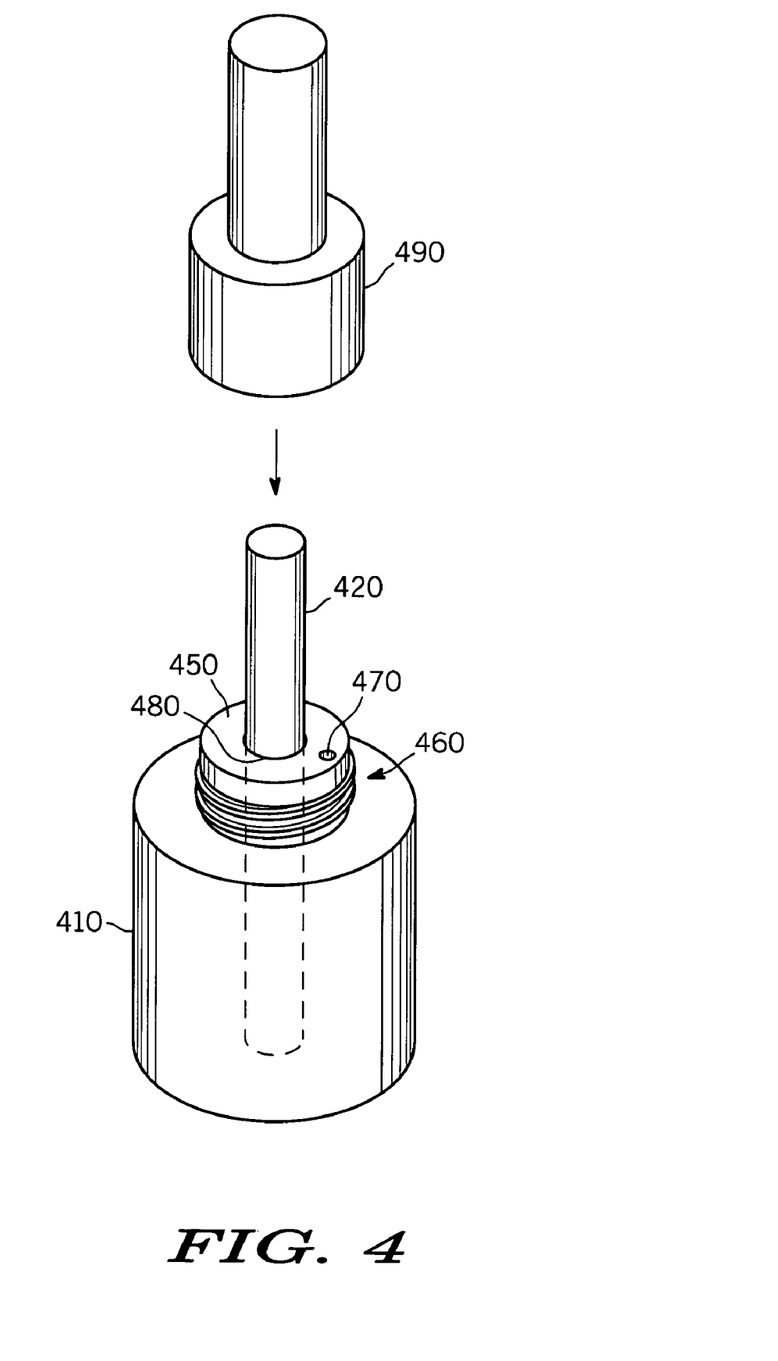
FIG. 4 contains an illustration of several of the components in accordance with one embodiment of the present invention.

With reference to the illustrations in FIG. 4, reservoir 410 may comprise a blow-molded plastic bottle with substantially round or bulb structure. Not to be limited to any particular configuration for closure 490, FIG. 4 depicts one embodiment of a threaded closure 490 which can engage by threads to the threaded neck 460 of bottle 410. The top portion of closure 490 is necessarily larger than the exposed portion of wick 420 protruding from bottle 410 so that engagement of the closure 490 onto bottle 410 will completely encase wick 420.

For the present invention, it is preferable to have wick 420 fit firmly into reservoir 410. This can be accomplished by way of a neck collar or fitment 450, which snaps snugly over neck 460 of bottle 410. Neck fitment 450 preferably contains an air vent hole 470 in addition to the opening 480 configured to tightly accept and engage the wick 420. Preferably the air vent hole 470 is very small, for example, about 0.010 inch in diameter, so that volatizable material 440 cannot drip out from it should the entire apparatus be inverted without closure 490 present. As mentioned above, dripping from air vent hole 470 can also be prevented by thickening the volatizable material, or by making the air vent hole 470 very small, or by a combination of the two. Closure 490 is expected to seal over air vent hole 470 in addition to encasing the wick 420. Removal of closure 490 from reservoir 410 will therefore expose both air vent hole 470 and wick 420. Air vent hole 470 provides pressure relief for the interior of reservoir 410 when the volatizable material delivery system is put into operation. For example, when volatizable material 440 is forced by capillary action up through wick 420, the air vent hole 470 will prevent an internal vacuum from developing inside reservoir 410 and will ensure atmospheric pressure is maintained inside reservoir 410, thus preventing the capillary action from slowing down over time. Not to be limited to any particular types of material, both neck fitment 450 and closure 490 can for example be manufactured from injected molded plastic such as polypropylene.

Although both shown as round shaped in FIG. 4, the neck 460 of reservoir 410, and the neck fitment 450, do not necessarily need to be round. This is only one embodiment, and it can be appreciated that the neck 460, neck fitment 450, and closure 490 can be configured into any shape, including square, triangular, etc. Additionally, the neck 460 can comprise any type of fastening mechanism to reversibly engage with closure 490. The threaded feature shown in FIG. 4 is only one embodiment, and it should be obvious to those skilled in the art that this closure 490 could simply snap onto neck 460 rather than thread onto it. The only requirement is that closure 490 seal reservoir 410 during merchandising, shipment, and storage, in order to prevent the inadvertent leakage of volatizable material 440 prior to removal of the closure.

Referring to FIG. 2, in one embodiment of the present invention the material delivery system 108 comprises reservoir 410, wick 420 and emanator 430, in communication. The dispersing of volatizable material 440 does not start until a connection is made between wick 420 and emanator 430. Wick 420 does not have sufficient exposed surface area to function as the surface for any substantial vaporization, although some minimum amount of vaporization is still expected from this short exposed wick portion. Emanator 430 facilitates dispersion of the material to the surrounding environment. In a preferred embodiment, the emanator 430 is positioned adjacent to one or more vents 104 in enclosure 102. The emanator is configured to be the volatilization platform for the volatizable material through judicial choice of its materials of composition and its size, as mentioned above.

Central to the present invention is a method for the user to activate the vapor-dispersing apparatus, which as explained above, means to connect wick 420 to emanator 430. Once the vapor-dispersing apparatus is activated, it is preferable to lock out access to the emanator 430 since it will quickly become saturated with volatizable material 440, a potential irritant or toxin, so it is beneficial to prevent further contact of emanator 430 once it has been saturated. A method of activation of the vapor-dispersing apparatus is part of the present invention and it is, in the simplest sense, the connecting together of wick 420 to emanator 430, thereby starting the movement of volatizable material 440 up through wick 420 and into emanator 430. As mentioned above, it is preferred that closure 490 be firmly engaged to reservoir 410 during merchandising, shipment and storage of the unit, so one additional step for activation is the removal of closure 490 from reservoir 410 prior to the connecting together of wick 420 with emanator 430.

Figure 5:
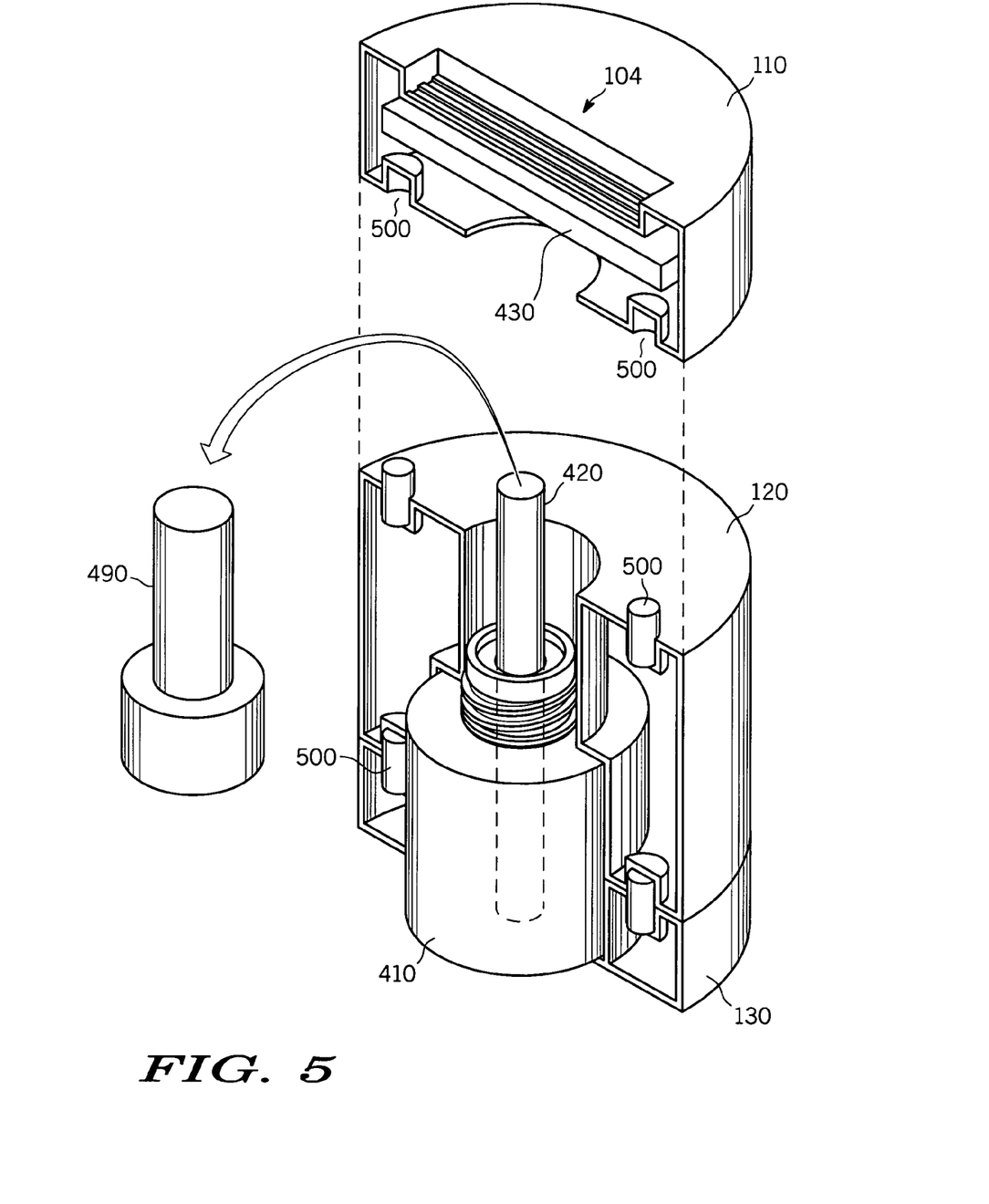
FIG. 5 is a cross-section of a vapor-dispersing apparatus in accordance with another embodiment of the present invention.

An additional embodiment of the present invention is depicted in FIG. 5. The housing portions 110, 120 and 130 show the 3-piece enclosure mentioned above and first depicted in FIG. 3. Additionally, a pre-assembly of housing portions 120 and 130 may be used to hold the material delivery system 108 minus the emanator 430. That is, in the embodiment depicted in FIG. 5, all of the components shown in FIG. 4 may be held in the sub-assembly comprising housing portions 120 and 130, including closure 490 that begins the activation process engaged with reservoir 410. The action shown in FIG. 5, that is, removal of closure 490 from reservoir 410 followed by the fitting together of top housing portion 110 to the remaining housing portions, constitutes activation of the apparatus because of the concomitant connecting together of the wick 420 to the emanator 430. Thus, the activation of the present invention comprises the steps of first, removal of closure 490 from reservoir 410, and second, the fitting of housing portion 110 to a pre-assembly of housing portions 120 and 130 to complete enclosure 102.

As mentioned previously, it is preferable not to be able to reopen the completed enclosure 102 and gain access to the emanator 430 once the apparatus has been activated and the emanator 430 is saturated with potentially hazardous volatizable material 440. To prevent reopening of the apparatus once activated, fasteners are incorporated into the present invention to irreversibly connect together the housing portions comprising the complete enclosure 102. Generic fasteners 500 are shown in the illustrations in FIGS. 5, 6 and 7a. These fasteners 500 provide a substantially irreversible fastening means for connecting together the housing portions that may comprise the complete enclosure 102.

Figure 6:
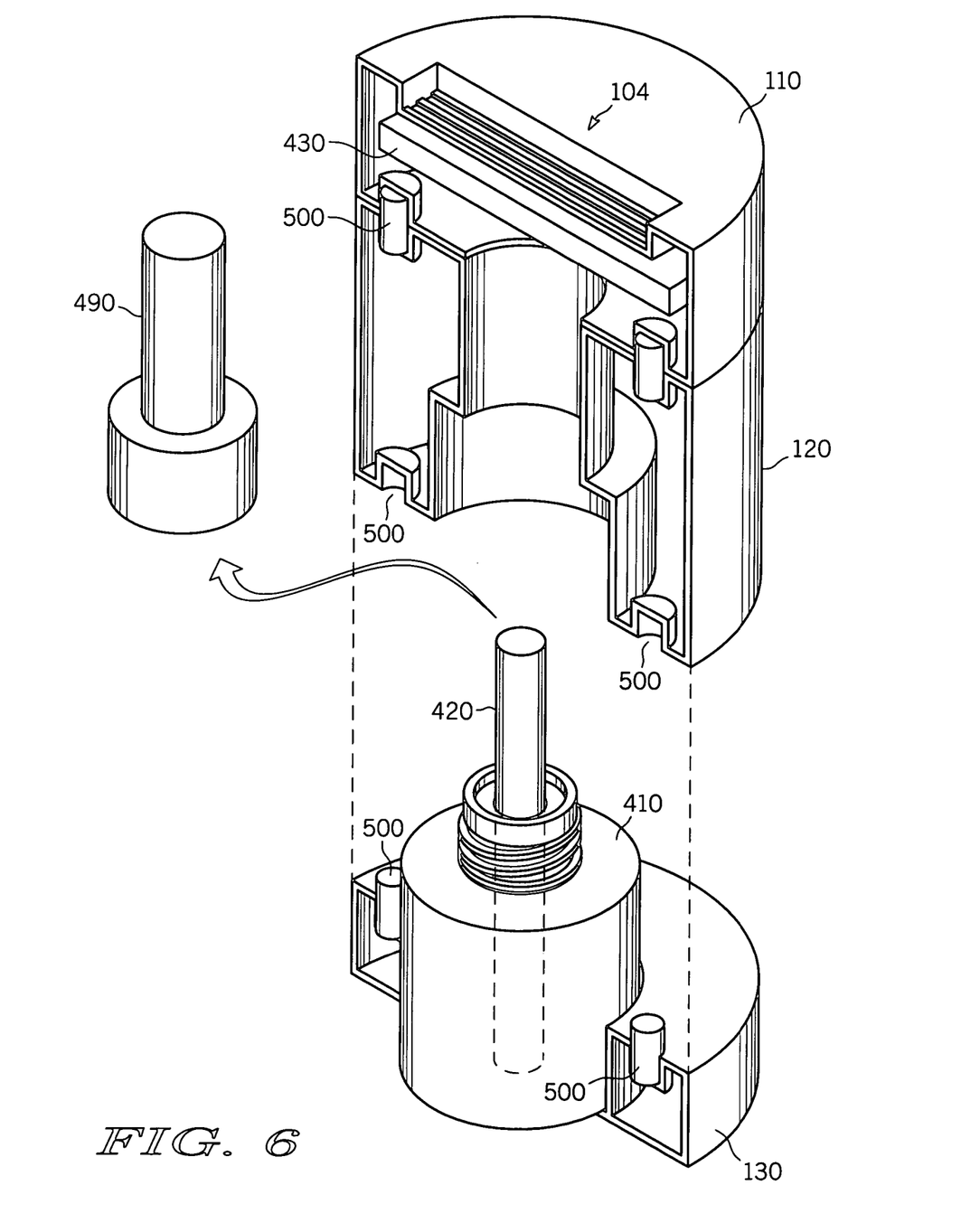
FIG. 6 is a cross-section of a vapor-dispersing apparatus in accordance with another embodiment of the present invention.
Figures 7A, 7B:
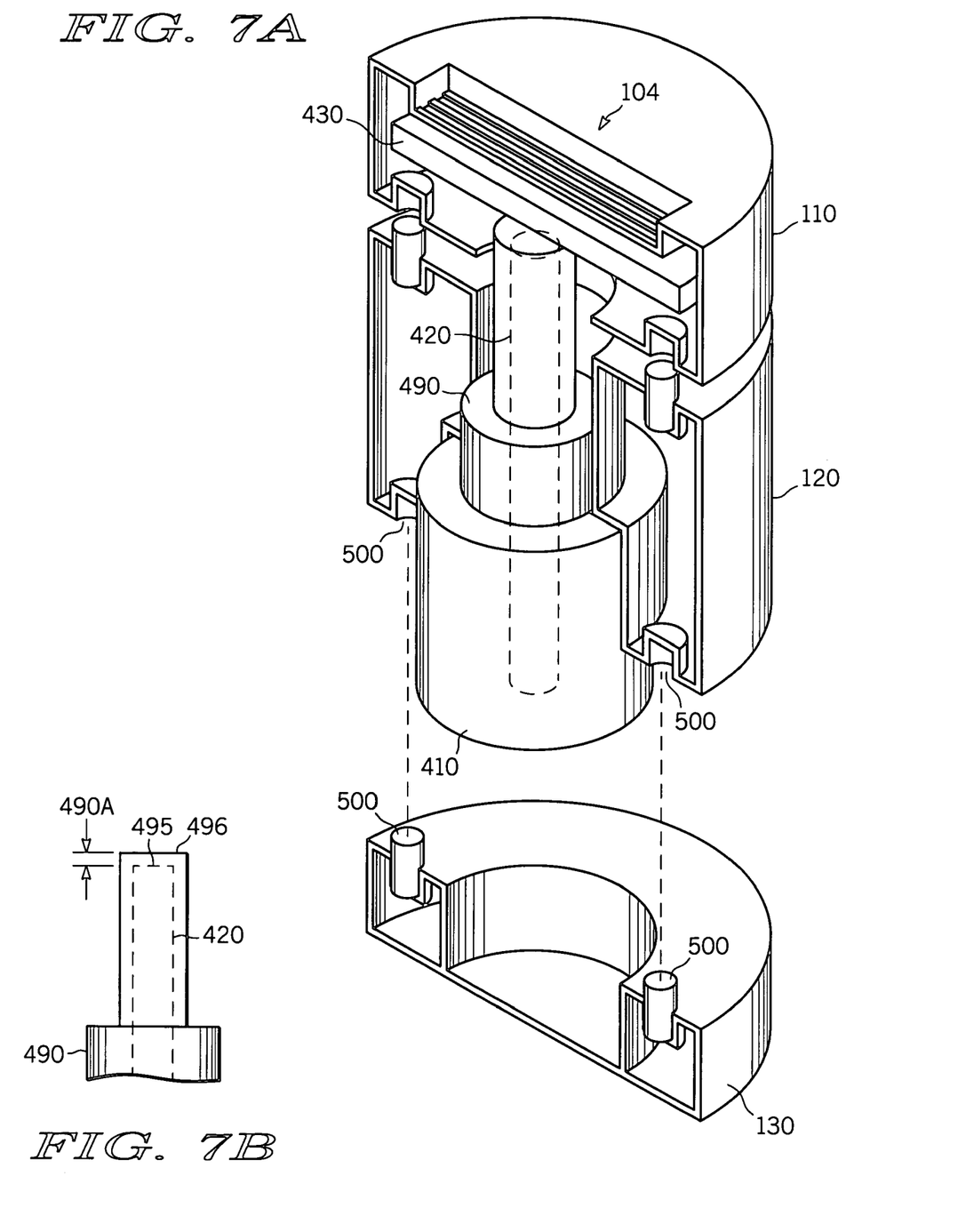
FIG. 7a is a cross-section of a vapor-dispersing apparatus in accordance with another embodiment of the present invention.
FIG. 7b contains an illustration detailing the dimensional relationship of several of the components used in one embodiment of the present invention.
Figure 8:
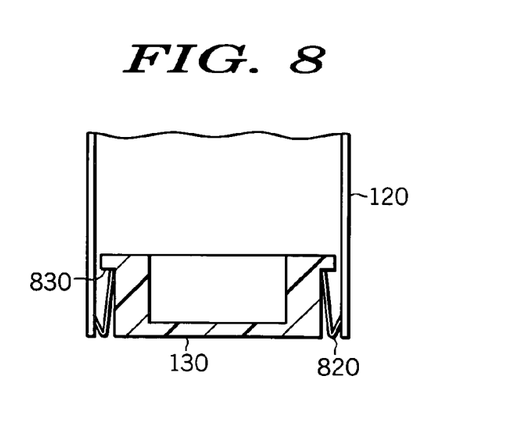
FIG. 8 contains an illustration of one embodiment of a fastening means used in the present invention.
Figure 9:
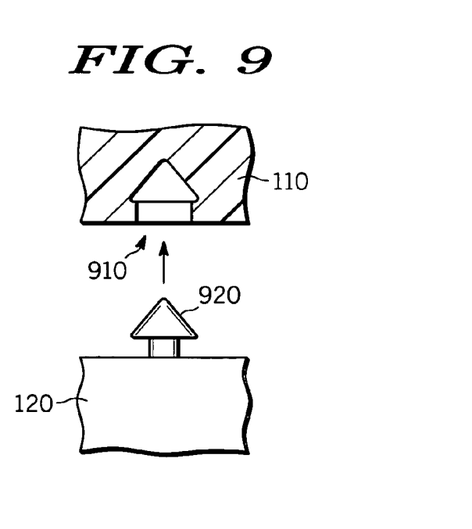
FIG. 9 contains an illustration of another embodiment of a fastening means used in the present invention.

Fasteners 500 are envisioned to comprise a wide range of configurations. For example, fasteners 500 could be as simple as plastic tabs locking into slots or detents. As shown in FIG. 8, housing portion 120 may lock together with housing portion 130 in a substantially irreversible manner if a folded tab 820 on housing portion 120 is configured to snap into a detent 830 configured into housing portion 130. It can be appreciated that various folded tabs and detents may be arranged and interchanged on the various housing portions as required for a specific embodiment. Or, the fasteners 500 may be much more sophisticated, for example, an arrow shaped molded protrusion of plastic that irreversibly snaps into a corresponding hole, whereby the bulb or arrow shaped end of the fastener cannot be backed out from the hole. This embodiment is shown in FIG. 9 wherein point 920 molded on housing portion 120 is configured to substantially irreversibly engage into hole 910 in housing portion 110. Whatever the precise nature of the fasteners 500, the important consideration is that the fasteners 500 are in pairs situated on adjacent positions of the housing portions such that they necessarily help to line up and connect together the enclosure 102. There can be any number of pairs of fasteners 500, even though the embodiments depicted in FIGS. 5, 6 and 7a show only four sets of fasteners, two pairs holding together the top 110 and middle 120 housing portions and two more pairs of fasteners 500 holding together the middle 120 and the bottom 130 housing portions. As mentioned above, any connecting together of any two housing portions is designed to be substantially irreversible, thus preventing access to the activated apparatus.

The present invention is unique in that it can be merchandized as a bundle of separate components appearing much like the complete apparatus, but actually comprising an unassembled apparatus that is not yet activated. This is accomplished by utilizing the closure 490 to a functional advantage beyond just sealing the reservoir 410. FIG. 7b illustrates that closure 490 is longer than wick 420. This is necessarily the case because closure 490 is used to encase the exposed end of wick 420 during the merchandising of the device. As shown in FIG. 7b, the length by which closure 490 extends beyond wick 420 is length 490A, that is, the distance measured from the top end 495 of wick 420 to the top end 496 of closure 490 is distance 490A. As shown in FIG. 7a, the length of closure 490 can be designed such that it prevents the fasteners 500 from engaging the top-housing portion 110 to the middle housing portion 120 provided the closure 490 remains on reservoir 410. In the embodiment depicted in FIG. 7a, if the closure 490 is on reservoir 410, the length of closure 490 will prevent the fasteners 500 from engaging and connecting together housing portion 110 with housing portion 120. The length 490A shown in FIG. 7b need not be very large, for example it may be only ⅛ inch to ½ inch in length, although this distance can really be any length practical. It is desirable not to have the user inadvertently assemble the apparatus without first removing closure 490 from reservoir 410, otherwise, if the fasteners indeed provide for irreversible connection, the apparatus will be useless with no way to open it again to correct the mistake. In this way, the additional height 490A that closure 490 provides beyond the length of the wick 420 is used to keep the set of fasteners 500 apart such that they cannot fasten together. Indeed, the only way to be able to fasten together the last housing portion to the remainder of the enclosure is to first remove the closure 490 from the reservoir 410. Then the wick 420 will be able to be positioned all the way up against emanator 430, thus allowing the fasteners 500 to come into contact with one another and to fasten.

Figure 10:
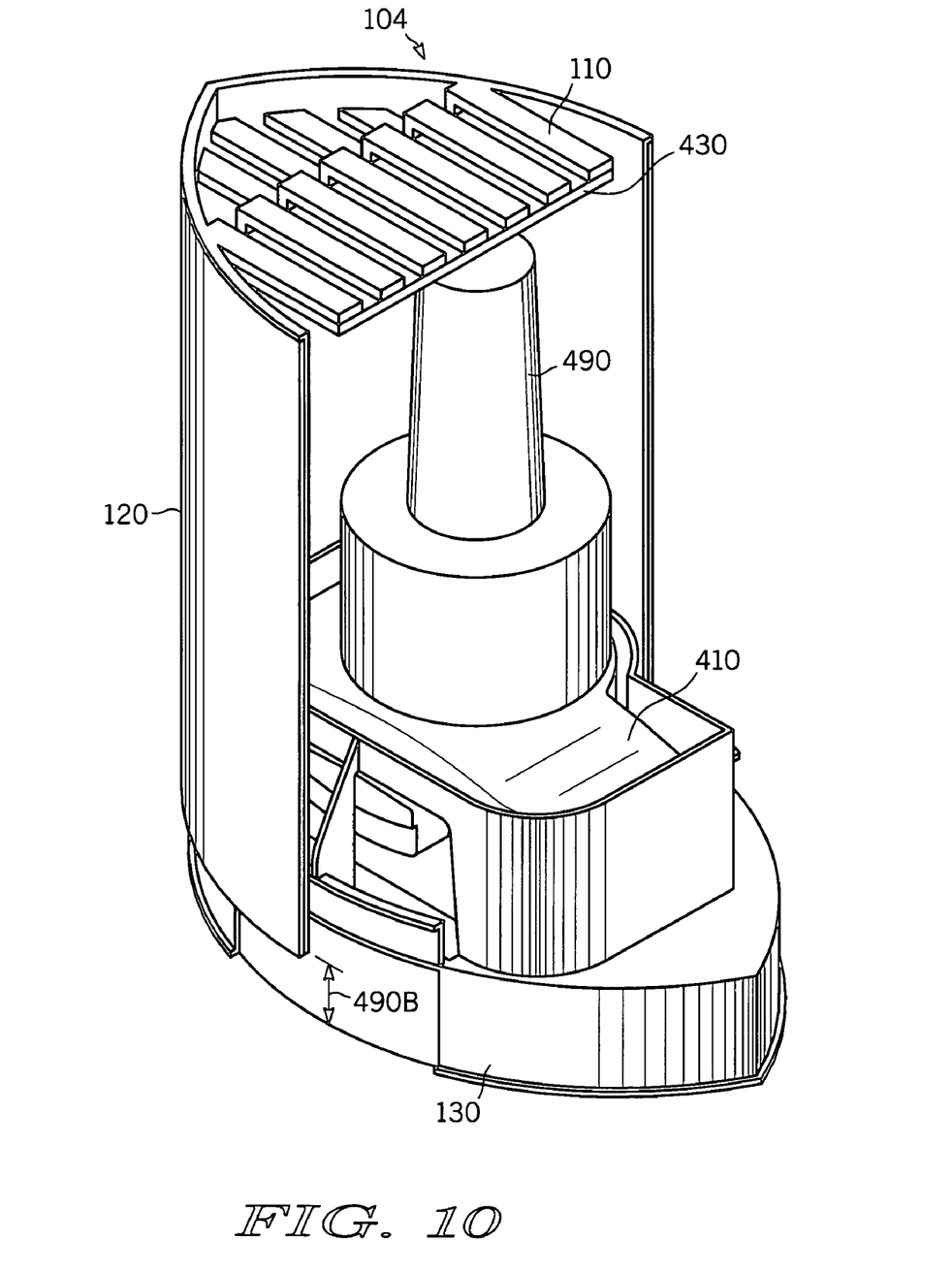
FIG. 10 is a cross-sectional perspective view of one embodiment of the device in the storage state.
Figure 11:
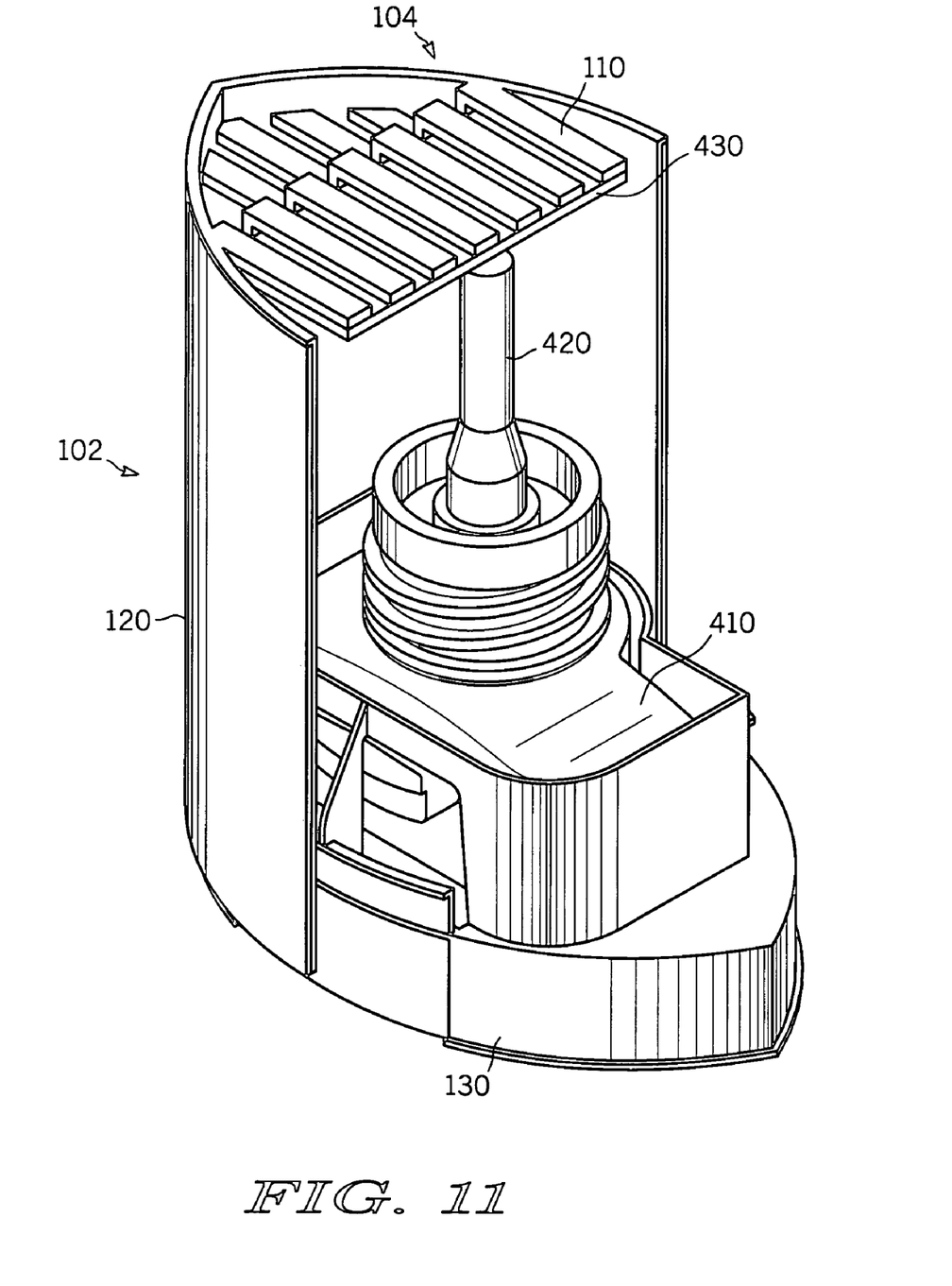
FIG. 11 is a cross-sectional perspective view of one embodiment of the device in the activated state.

This is more clearly shown by referring to the embodiment in FIGS. 10 and 11. In FIG. 10, the closure 490 touches the emanator 430 and consequently, the bottom housing portion 130 is prevented from fully engaging with middle housing portion 120. A gap 490B exists since the closure 490 prevents the bottom housing portion 130 from engaging any further with middle housing portion 120. The dimension 490A illustrated in FIG. 7b is translated to gap 490B, that is, they are the same length. In contrast, FIG. 11 shows the activated device without closure 490, (the closure having been removed and discarded and is therefore not shown), and now the bottom housing portion 130 may be fully engaged with middle housing portion 120, gap 490B is gone, and now wick 420 contacts emanator 430. Thus, once the closure 490 is removed, the device can be fully assembled and activated.

As shown in FIGS. 5, 6, 7a, 10 and 11, the emanator 430 is held in housing portion 110, primarily for convenience to the user and also to guarantee that it is in the correct position, such as near the vent(s) 104, when the device is activated. In this embodiment, it is assumed that the vent or vents 104 are configured somewhere on the top housing portion 110, although there could be additional vents in either housing portion 120 or 130, or both, in order to maximize air flow through the unit and across the emanator 430. Vents in all housing portions could provide a flow-thru ventilation scheme, which may maximize evaporation of the volatizable material 440 off emanator 430. Emanator 430 can be clipped into top housing portion 110 so that it does not fall out prior to assembly and activation of the apparatus. If the emanator 430 is relatively thin cellulose, it can be tucked under one or more retaining tabs configured inside housing portion 110 so that it is pressed up against vent(s) 104 and held such that it will not inadvertently fall out. During manufacturing, housing portions 120 and 130 can already be fastened together as a pre-assembly, or they may comprise a single housing portion, that is 120 and 130 may actually comprise one housing with bottom and sides but no top. The important feature is that the user completes the assembly of the enclosure 102, whether it is the fastening of one part to another, for example, putting the top onto an enclosure already having sides and bottom, or fastening one part to a pre-assembly of more than one part. This connecting together of the remaining portion of the enclosure 102 will necessarily activate the unit by connecting together wick 420 to emanator 430 at a predetermined position and a predetermined pressure.

When the vapor-dispersing device is activated, it is preferable to have the wick 420 in connection with the emanator 430 at a predetermined position and pressure. For example, for speed of saturation of emanator 430 with volatizable material 440, the logical connection point for wick 420 onto emanator 430 would be about the geometric center of the emanator 430. This is easily accomplished by configuring reservoir 410 to firmly fit into housing portion 130, or into a single housing such as defined by 120 and 130 together, and to have the emanator 430 firmly held into remaining top housing portion 110. In this way, connecting together the last housing portion 110 to the remaining housing portion or portions, will necessarily line up wick 420 to emanator 430 at the correct position and pressure. The desirable pressure between the tip of wick 420 and emanator 430 is firm enough to prevent their coming apart during movement or handling of the activated unit, but light enough so as not to damage the top of the unit, for example, by forcing or bowing out a grill section that may comprise vents 104. The dimension for the sides of the enclosure 102, the length of the exposed end of wick 420, and the position of the emanator 430 in the top housing portion 110, all work to position the wick at the correct position and pressure against emanator 430 when the enclosure 102 is fully assembled.

In another embodiment of the present invention shown in FIG. 6, housing portion 130 is shown as the last remaining housing portion needed in completing the full enclosure 102. In this embodiment, the middle housing portion 120 and top housing portion 110 may be supplied as a pre-assembly or as a single entity, and it is the bottom housing portion 130 that is separately provided with enclosure 490 protecting the wick 420 in reservoir 410. Thus, it is the bottom housing portion 130 that is attached to complete the enclosure 102 and activate the apparatus. The embodiment shown in FIG. 6 has a small advantage over the embodiment shown in FIG. 5 in that having the reservoir 410 fitted into a separate bottom housing 130 allows for more easy access to the closure 490. Additionally, with the emanator 430 way up inside the top of a subassembly or single entity comprising portions 110 and 120, there is no way for the user to play with the emanator 430 and cause it to prematurely fall out of the unit prior to snapping together of the portions and activation of the apparatus. For the embodiment depicted in FIG. 6, the method of activation of the apparatus is for the closure 490 to be removed from the reservoir 410 and for the bottom housing portion 130 to be irreversibly snapped onto the remaining housing portions to complete enclosure 102 and start the flow of volatizable material 440 from reservoir 410 to emanator 430.

In the embodiment shown in FIG. 6, the reservoir 410 would preferentially fit substantially firmly into the bottom housing portion 130. It is advantageous not to have the reservoir inadvertently separate from the bottom housing portion 130 from where it could be misused. In this way, the bottom housing portion 130 functions as a sort of tray for the reservoir 410. As in the embodiment of FIG. 5, the apparatus of FIG. 6 must also fasten together irreversibly such that the user cannot gain access to the saturated emanator 430. Thus, the fasteners 500 depicted in FIG. 6 should irreversibly fasten together bottom housing portion 130 with the remaining housing portions to form an integral enclosure 102 that can no longer be opened.

Figure 12:
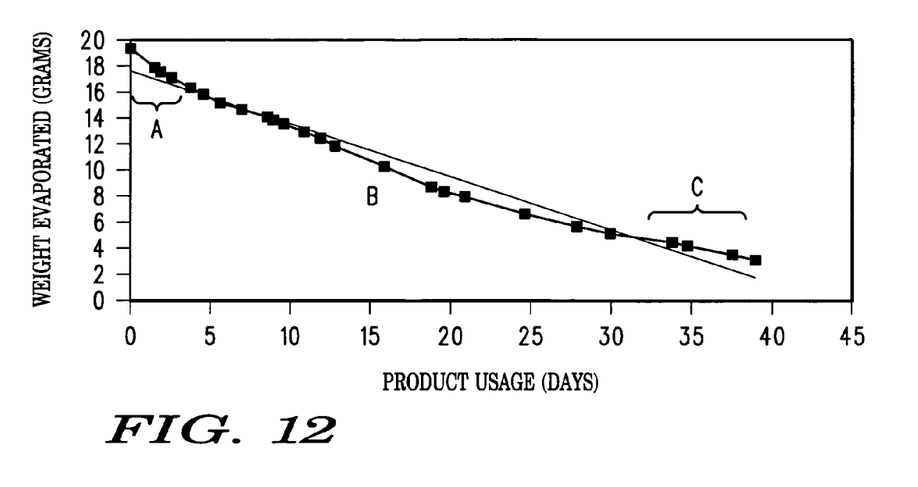
FIG. 12 is a graph showing quantitatively the weight loss (in grams) over time (in days) for an exemplary vapor-dispersing apparatus in accordance with one embodiment of the present invention.

As mentioned above, one embodiment of the present invention is a vapor-dispersing apparatus with both rapid activation and substantially linear delivery of volatizable material, made possible by the rapid wicking of volatizable material 440 through wick 420 to generate a substantially saturated emanator 430, and the subsequent evaporation of volatizable material from the substantially saturated emanator 430, respectively. In the context of an air freshener, both the rapid activation and the linear delivery of volatizable material 440 (i.e., fragrance) are highly desirable features to the consumer. As shown in FIG. 12, weight loss (in grams), from one embodiment of the present invention comprising scented fragrance oil is near linear throughout a significant portion of the life of the device (section "B" on the graph). As also evident in FIG. 12, weight loss is rapid in the first few days (section "A" on the graph), demonstrating the rapid activation feature of the invention, and then substantially linear (section "B") until a few grams of material remain in the device (section "C"), when the device finally slows down.

We claim:

1. A vapor-dispersing apparatus comprising:
   a. an enclosure further comprising top, middle, and bottom housing portions;
   b. at least one vent in said top housing portion;
   c. an emanator within said enclosure and positioned at said vent;
   d. a material delivery system within said enclosure, said system further comprising a bottle with an opening fitted with a wick and containing a volatizable material, said wick covered with a closure secured to said bottle; and,
   e. a fastening means to provide a substantially irreversible connections between said top, and middle housing portions, and between said middle and bottom housing portions;
   f. wherein said apparatus is activated by first removing said closure from said bottle to expose said wick, then substantially irreversibly connecting together a subassembly comprised of said top and middle housing portions to said bottom housing portion, or a subassembly comprised of said bottom and middle housing portions to said top portion, to simultaneously complete the assembly of said enclosure, and to put said wick into physical contact with said emanator; and,
   g. wherein said fastening means comprise small folded tabs configured on the inside of both ends of said middle housing portion such that each tab snaps into detents configured on said top and bottom housing portions when said closure is removed from said bottle and said housing portions are fully engaged together.

2. The vapor dispersing apparatus of claim 1, wherein said volatizable material comprises a high intensity fragrance component.

3. The vapor-dispersing apparatus of claim 1, wherein said wick comprises porous plastic having average pore size of from about 20 microns to about 100 microns.

4. The vapor-dispersing apparatus of claim 1, wherein said emanator is constructed from material selected from the from consisting of paper, cellulose, cotton, non-wovens, ceramic, compressed polymer fibers, wood, and porous plastic sheeting, and mixtures thereof.

5. The vapor-dispersing apparatus of claim 4, wherein said emanator comprises a cellulose pad measuring from about 1 sq. inch to about 2 sq. inches and from about ⅛ inch to about ⅜ inch thick.

6. The vapor-dispersing apparatus claim 1, wherein said bottle further includes a neck fitment, said neck fitment comprising an air vent and opening, said opening configured to engage said wick, bottle configured to contain said volatizable material.

7. The vapor-dispersing apparatus of claim 1, wherein said bottle fits and is held into said bottom housing portion, anti said emanator fits and is held into said top housing portion.

8. The vapor-dispersing apparatus of claim 1, wherein at least one of said bottom and said middle housing portions comprises a viewing structure enabling view of the remaining amount of said volatizable material.

9. The vapor-dispersing apparatus of claim 1, wherein said closure on said bottle is configured to be front about ⅛ inch to about ½ inch longer than the length of extension of Said wick from said bottle, in order to prevent engagement of a subassembly comprising said bottom and middle housing portions to said top housing portion, or a subassembly comprising said top and middle housing portions to said bottom housing portion, unless said closure is first removed front said bottle.

* * * * *